United States Patent [19]

Maubru

[11] Patent Number: 5,735,909
[45] Date of Patent: *Apr. 7, 1998

[54] COMPOSITIONS AND PROCESSES FOR THE OXIDATION DYEING OF KERATIN FIBRES WITH AN OXIDATION BASE, A META-AMINOPHENOL COUPLER, AND A 6-HYDROXYINDOLINE COUPLER

[75] Inventor: Mireille Maubru, Chatou, France

[73] Assignee: L'Oreal, Paris, France

[*] Notice: The term of this patent shall not extend beyond the expiration date of Pat. No. 5,620,484.

[21] Appl. No.: 607,857

[22] Filed: Feb. 27, 1996

[30] Foreign Application Priority Data

Feb. 27, 1995 [FR] France ................. 95 02272

[51] Int. Cl.$^6$ ............................. A61K 7/13
[52] U.S. Cl. ...................... 8/412; 8/409; 8/410
[58] Field of Search ................ 8/406, 408, 409, 8/410, 412, 416, 421, 423

[56] References Cited

U.S. PATENT DOCUMENTS

| | | | |
|---|---|---|---|
| 3,649,160 | 3/1972 | Kalopissis et al. | 8/409 |
| 4,013,404 | 3/1977 | Parent et al. | 8/423 |
| 5,061,289 | 10/1991 | Clausen et al. | 8/406 |
| 5,131,911 | 7/1992 | Lang et al. | 8/406 |
| 5,207,798 | 5/1993 | Cotteret et al. | 8/408 |
| 5,354,870 | 10/1994 | Lang et al. | 548/469 |
| 5,380,340 | 1/1995 | Neunhoeffer et al. | 8/409 |
| 5,391,206 | 2/1995 | Cotteret | 8/408 |

FOREIGN PATENT DOCUMENTS

| | | |
|---|---|---|
| A-0375977 | 7/1990 | European Pat. Off. . |
| A-0428441 | 5/1991 | European Pat. Off. . |
| A-0446132 | 9/1991 | European Pat. Off. . |
| A-0465339 | 1/1992 | European Pat. Off. . |
| A-0465340 | 1/1992 | European Pat. Off. . |
| A-0634164 | 1/1995 | European Pat. Off. . |
| A-1916139 | 11/1969 | Germany . |
| A-3031709 | 4/1982 | Germany . |
| A-3743769 | 7/1989 | Germany . |
| A-3930446 | 3/1990 | Germany . |
| A-4133957 | 4/1993 | Germany . |
| A-1217479 | 12/1970 | United Kingdom . |
| A-2180215 | 3/1987 | United Kingdom . |
| WO-A-9309759 | 5/1993 | WIPO . |
| WO-A-9408970 | 4/1994 | WIPO . |

OTHER PUBLICATIONS

English Derwent Abstract of DE–A–3743769, Jul. 1989.
English Derwent Abstract of DE–A–3031709, Apr. 1982.
English Derwent Abstract of EP–A–0634164, Jan. 1995.
English Derwent Abstract of EP–A–0428441, May 1991.
English Derwent Abstract of EP–A–0465339, Jan. 1992.
English Derwent Abstract of WO–A–9408970, Apr. 1994.

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

A composition for the oxidation dyeing of keratin fibres, in particular human keratin fibres such as the hair, comprising at least one suitably selected oxidation base, at least one meta-aminophenol or an acid addition salt thereof as a first coupler, and at least one 6-hydroxyindoline or an acid addition salt thereof as a second coupler, and to the dyeing process using this composition with an oxidizing agent.

21 Claims, No Drawings

COMPOSITIONS AND PROCESSES FOR THE OXIDATION DYEING OF KERATIN FIBRES WITH AN OXIDATION BASE, A META-AMINOPHENOL COUPLER, AND A 6-HYDROXYINDOLINE COUPLER

The present invention is directed to a composition for the oxidation dyeing of keratin fibres, in particular human keratin fibres such as the hair, comprising at least one suitably selected oxidation base, preferably selected from para-phenylenediamines, acid addition salts of para-phenylenediamines, bis(phenyl)alkylenediamines, and acid addition salts of bis(phenyl)alkylenediamines, at least one first coupler selected from meta-aminophenols and acid addition salts of meta-aminophenols, and at least one second coupler selected from 6-hydroxyindoline and the acid addition salts thereof, and to the dyeing process using this composition with an oxidizing agent.

It is known to dye keratin fibres, and in particular human hair, with dye compositions containing oxidation dye precursors, in particular ortho- or para-phenylenediamines and ortho- or para-aminophenols, which are generally referred to as oxidation bases. The oxidation dye precursors, or oxidation bases, are colorless or weakly colored compounds which, when combined with oxidizing products, may give rise to colored compounds and dyes by a process of oxidative condensation.

It is also known that the shades obtained with these oxidation bases may be varied by combining them with couplers or coloration modifiers, the latter being chosen in particular from aromatic meta-diamines, meta-aminophenols, meta-diphenols and certain indole or indoline compounds.

The variety of molecules used as oxidation bases and couplers makes it possible to obtain a wide range of colors.

The so-called "permanent" coloration obtained by means of these oxidation dyes must moreover satisfy a certain number of requirements. Thus, the dyes must have no toxicological drawbacks, and they must allow shades of the desired strength to be obtained and have good resistance to external agents, such as light, inclement weather, washing, permanent waving, perspiration and friction.

The dyes must also allow white hairs to be covered and, lastly, they must be as unselective as possible, that is to say that they must allow the smallest possible differences in coloration to be produced over the entire length of the same keratin fibre, which may indeed be differently sensitized (i.e. damaged) between its tip and its root. In other words, it is desired to have dyes which produce coloration of low selectivity.

In order to produce natural shades or shades with glints, it is common to use dye compositions comprising a para-phenylene-diamine derivative as an oxidation base and a meta-aminophenol derivative as a coupler. However, the colorations obtained with such dye compositions are not entirely satisfactory since they generally exhibit high selectivity.

Moreover, compositions for the oxidation dyeing of keratin fibres in alkaline medium, comprising at least one oxidation base such as, for example, para-phenylenediamine or a para-phenylenediamine derivative in combination with an indole coupler such as, for example, 6-hydroxyindoline, have already been proposed, in particular in French Patent Application FR 2,008,797, the disclosure of which is incorporated herein by reference. These compositions are not entirely satisfactory either, since they lead to colorations which also exhibit high selectivity.

Now, the inventor has discovered that it is possible to obtain novel dyes in acidic, neutral or alkaline medium, which are capable of giving rise to powerful colorations which are less selective, i.e., have lower selectivity, than the colorations of the prior art, and which show good resistance to the various attacking factors to which the hair may be subjected, by combining at least one suitably selected oxidation base, preferably selected from para-phenylenediamines, acid addition salts of para-phenylenediamines, bis(phenyl)alkylenediamines, and acid addition salts of bis(phenyl)alkylenediamines, at least one first coupler selected from meta-aminophenols and acid addition salts of meta-aminophenols, and at least one second coupler selected from 6-hydroxyindoline and the acid addition salts thereof.

This subject forms the basis of the present invention.

A first subject of the invention is thus a composition for the oxidation dyeing of keratin fibres, and in particular human keratin fibres such as the hair, which comprises, in a medium which is suitable for dyeing:

at least one suitably selected oxidation base, preferably selected from para-phenylenediamines, acid addition salts of para-phenylenediamines, bis(phenyl)alkylenediamines, and acid addition salts of bis(phenyl)alkylenediamines, at least one first coupler selected from meta-aminophenols and acid addition salts of meta-aminophenols, and at least one second coupler selected from 6-hydroxyindoline and the add addition salts thereof.

The oxidation dyeing composition in accordance with the invention makes it possible to obtain powerful colorations in varied shades, which are quite unselective and have excellent properties of resistance both to atmospheric agents such as light and inclement weather and to perspiration and the various treatments to which the hair may be subjected, such as shampooing and permanent waving.

Another subject of the invention is a process for the oxidation dyeing of keratin fibres using this composition.

Among the meta-aminophenols which may preferably be used as a first coupler in the compositions in accordance with the invention, mention may be made of the compounds corresponding to formula (I) and the acid addition salts thereof:

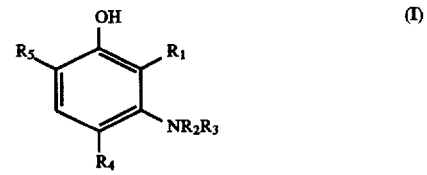

in which:

$R_1$ and $R_4$, which may be identical or different, represent a hydrogen or halogen atom or a $C_1$–$C_4$ alkyl or $C_1$–$C_4$ alkoxy radical, $R_2$ represents a hydrogen atom or a $C_1$–$C_4$ alkyl, $C_1$–$C_4$ monohydroxyalkyl, $C_2$–$C_4$ polyhydroxyalkyl, $C_1$–$C_4$ trifluoroalkyl or carbamoylmethyl radical, $R_3$ represents a hydrogen atom or a $C_1$–$C_4$ alkyl radical or forms, with $R_2$ and the nitrogen atom, a 5- or 6-membered heterocycle, and $R_5$ represents a hydrogen or halogen atom or a $C_1$–$C_4$ alkyl, $C_1$–$C_4$ alkoxy, $C_1$–$C_4$ monohydroxyalkyl or $C_2$–$C_4$ polyhydroxyalkyl radical.

Among the meta-aminophenols of above formula (I) which may preferably be used as a first coupler in the dye compositions in accordance with the invention, mention may be made of 3-aminophenol, 5-amino-2-methoxyphenol, 5-amino-4-chloro-2-methylphenol, 5-amino-2,4-dimethoxyphenol, 5-amino-2-β-hydroxyethyloxyphenol, 5-N-(β-hydroxyethyl)amino-4-methoxy-2-methylphenol, 5-amino-4-methoxy-2-methylphenol, 5-N-(γ-hydroxypropyl)amino-2-methylphenol, 5-N-(β-hydroxyethyl)amino-2-methylphenol, 5-amino-2-methylphenol, 3-N-(carbamoylmethyl)aminophenol, 5-N-(carbamoylmethyl)amino-2-methylphenol, 3-N,N-(dimethyl)aminophenol, 3-N,N-(diethyl)aminophenol, 3-amino-2,4-dichlorophenol, 3-amino-4,6-dichlorophenol, 5-amino-6-chloro-2-methylphenol, 2-chloro-5-N-(2',2',2'-trifluoroethyl)aminophenol, 5-amino-4-chloro-2-methylphenol, 3-N-(cyclopentyl)aminophenol, and the acid addition salts thereof.

Among the para-phenylenediamines which may preferably be used as an oxidation base in the compositions in accordance with the invention, mention may be made of the compounds corresponding to formula (II) and the acid addition salts thereof:

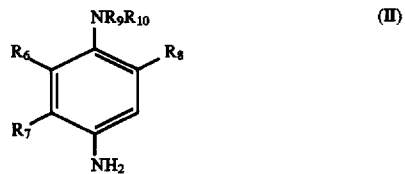

in which:

$R_6$, $R_7$ and $R_8$, which may be identical or different, represent a hydrogen or halogen atom or a $C_1$-$C_4$ alkyl, $C_1$-$C_4$ alkoxy, sulpho, carboxyl, $C_1$-$C_4$ monohydroxyalkyl or $C_2$-$C_4$ polyhydroxyalkyl radical, $R_9$ and $R_{10}$, which may be identical or different, represent a hydrogen atom, a $C_1$-$C_4$ alkyl, $C_1$-$C_4$ monohydroxyalkyl, $C_2$-$C_4$ polyhydroxyalkyl, ($C_1$-$C_4$) alkoxy($C_1$-$C_4$)alkyl, $C_1$-$C_4$ carbamylalkyl, $C_1$-$C_4$ mesylaminoalkyl, $C_1$-$C_4$ acetylaminoalkyl, $C_1$-$C_4$ ureidoalkyl, ($C_1$-$C_4$)carbalkoxy($C_1$-$C_4$)aminoalkyl, $C_1$-$C_4$ sulphoalkyl, $C_1$-$C_4$ piperidinoalkyl, $C_1$-$C_4$ morpholinoalkyl or phenyl radical or a phenyl radical substituted in the para position with an amino group, or $R_9$ and $R_{10}$ may together form, with the nitrogen atom to which they are attached, a piperidino or morpholino heterocycle;

it being understood that if $R_9$ and $R_{10}$ do not simultaneously represent a hydrogen atom, then at least one of the radicals $R_6$ and $R_8$ must represent a hydrogen atom.

Among the $C_1$-$C_4$ alkyl and $C_1$-$C_4$ alkoxy radicals of the above formulae (I) and (II), those which may more preferably be mentioned are the methyl, ethyl, propyl, methyloxy and ethyloxy radicals.

Among the para-phenylenediamines of above formula (II) which may more preferably be used as an oxidation base in the dye compositions in accordance with the invention, mention may be made of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 4-amino-N-ethyl-N-(carbamylmethyl)aniline, 4-amino-3-methyl-N-ethyl-N-(carbamylmethyl)aniline, 4-amino-N-ethyl-N-(β-piperidinoethyl)aniline, 4-amino-3-methyl-N-ethyl-N-(β-piperidinoethyl)aniline, 4-amino-N-ethyl-N-(β-morpholinoethyl)aniline, 4-amino-3-methyl-N-ethyl-N-(β-morpholinoethyl)aniline, 4-amino-N-ethyl-N-(β-acetylaminoethyl)aniline, 4-amino-N-(β-methoxyethyl)aniline, 4-amino-3-methyl-N-ethyl-N-(β-acetylaminoethyl)aniline, 4-amino-N-ethyl-N-(β-mesylaminoethyl)aniline, 4-amino-3-methyl-N-ethyl-N-(β-mesylaminoethyl)aniline, 4-amino-N-ethyl-N-(β-sulphoethyl)aniline, 4-amino-3-methyl-N-ethyl-N-(β-sulphoethyl)aniline, N-[(4'-amino)phenyl]morpholine, N-[(4'-amino)phenyl]piperidine, 2-β-hydroxyethyl-para-phenylenediamine, 2-fluoro-para-phenylenediamine, 2-carboxy-para-phenylenediamine, 2-sulpho-para-phenylenediamine, 2-isopropyl-para-phenylenediamine, 2-n-propyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, and the addition salts thereof with an acid.

Among the para-phenylenediamines of above formula (II) which may more preferably be used as an oxidation base in the dye compositions in accordance with the invention are para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine and 4-amino-N-(β-methoxyethyl)aniline and the acid addition salts thereof.

Among the bis(phenyl)alkylenediamines which may more preferably be used as an oxidation base in the dye compositions in accordance with the invention, mention may be made of the compounds corresponding to formula (III) and the acid addition salts thereof:

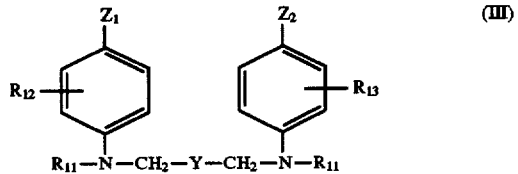

in which:

$Z_1$ and $Z_2$, which may be identical or different, represent a hydroxyl radical or a radical $NHR_{14}$ in which $R_{14}$ represents a hydrogen atom or a $C_1$-$C_4$ alkyl radical, $R_{11}$ independently represents a hydrogen atom, a $C_1$-$C_4$ alkyl, $C_1$-$C_4$ monohydroxyalkyl or $C_2$-$C_4$ polyhydroxyalkyl radical or a $C_1$-$C_4$ aminoalkyl radical in which the amino residue may be substituted, $R_{12}$ and $R_{13}$, which may be identical or different, represent a hydrogen or halogen atom or a $C_1$-$C_4$ alkyl radical, Y represents a radical, the radical being —$(CH_2)_n$—; —$(CH_2)_m$—O—$(CH_2)_m$—; —$(CH_2)_m$—CHOH—$(CH_2)_m$— or

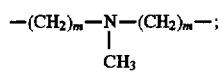

in which n is an integer ranging from 0 to 8 inclusively and m is independently an integer ranging from 0 to 4 inclusively.

Among the $C_1$–$C_4$ alkyl radicals of the above formula (III) which may preferably be mentioned are the methyl, ethyl and propyl radicals.

Among the bis(phenyl)alkylenediamines of above formula (III) which may preferably be used as an oxidation base in the dye compositions in accordance with the invention, mention may be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine and the acid addition salts thereof.

Among these bis(phenyl)alkylenediamines of formula (III), N, N'-bis(β-hydroxyethyl)-N,N'-bis(4'-aminophenyl)-1,3-diaminopropanol is more particularly preferred.

The acid addition salts which may be used in the context of the dye compositions of the invention are preferably chosen from the hydrochlorides, hydrobromides, sulphates and tartrates.

The oxidation base or bases in accordance with the invention, that is to say the para-phenylenediamine(s) and/or the bis(phenyl)alkylenediamine(s), preferably represent approximately from 0.0005 to 12% by weight relative to the total weight of the dye composition, and even more preferably approximately from 0.005 to 6% by weight relative to this weight.

The meta-aminophenol(s) of formula (I) which are used as a first coupler in the dye compositions in accordance with the invention, preferably represent approximately from 0.0001 to 10% by weight relative to the total weight of the dye composition, and even more preferably approximately from 0.005 to 5% by weight relative to this weight.

The 6-hydroxyindoline and/or the acid addition salt or salts thereof which are used as a second coupler in the dye compositions in accordance with the invention, preferably represent approximately from 0.0001 to 5% by weight relative to the total weight of the dye composition, and even more preferably approximately from 0.005 to 3% by weight relative to this weight.

The appropriate/suitable medium for the dyeing (or the support) generally comprises water or a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monomethyl ether and monoethyl ether, as well as aromatic alcohols such as benzyl alcohol or phenoxyethanol, similar products and mixtures thereof.

The solvents may be present in proportions preferably ranging approximately from 1 to 40% by weight relative to the total weight of the dye composition, and even more preferably approximately from 5 to 30% by weight.

The pH of the dye composition in accordance with the invention generally ranges from 3 to 12. The pH may be adjusted to the desired value using acidifying or basifying agents usually used in the dyeing of keratin fibres.

Among the acidifying agents which may preferably be mentioned, by way of example, are inorganic or organic adds such as hydrochloric add, orthophosphoric acid, carboxylic acids such as tartaric acid, citric acid and lactic acid, and sulphonic acids.

Among the basifying agents which may preferably be mentioned, by way of example, are aqueous ammonia, alkaline carbonates, alkanolamines such as mono-, di- and triethanolamines and derivatives thereof, sodium hydroxide, potassium hydroxide and the compounds of formula (IV):

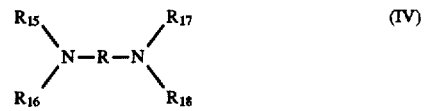

in which R is a propylene residue which may be substituted with a hydroxyl group or a $C_1$–$C_4$ alkyl radical; $R_{15}$, $R_{16}$, $R_{17}$ and $R_{18}$, which may be identical or different, represent a hydrogen atom or a $C_1$–$C_4$ alkyl or $C_1$–$C_4$ hydroxyalkyl radical.

In addition to the dyes defined above, the dye composition in accordance with the invention may also contain other oxidation bases and/or other couplers and/or direct dyes in order to modify the shades or to enrich them with glints.

The dye composition according to the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Obviously, a person skilled in the art will take care to choose this or these optional complementary compound(s) such that the advantageous properties intrinsically associated with the ternary combination in accordance with the invention are not, or are substantially not, adversely affected by the addition or additions envisaged.

The dye composition according to the invention may be in various forms, such as in the form of liquids, creams, gels or any other form which is suitable for dyeing keratin fibres, and in particular human hair.

Still another subject of the invention is a process for dyeing keratin fibres, and in particular human keratin fibres such as the hair, using the dye composition as defined above.

According to this process, at least one dye composition as defined above is applied to the fibres, the color being developed at acidic, neutral or alkaline pH using an oxidizing agent which is added to the dye composition either at the time of use or which is present in an oxidizing composition that is applied simultaneously or sequentially in a separate manner, i.e., the oxidizing composition is applied from a separate dispenser than the dye composition either at the same time as the dye composition, i.e., simultaneously, or sequentially with it.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for preferably from 3 to 50 minutes approximately, and more preferably from 5 to 30 minutes approximately, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may preferably be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably varies approximately from 3 to 12 and even more preferably from 5 to 11. The pH is adjusted to the desired value using acidifying or basifying agents usually used in the dyeing of keratin fibres and as defined above.

The oxidizing composition as defined above may also include various adjuvants used conventionally in compositions for dyeing the hair as defined above.

The composition which is finally applied to the keratin fibres may be in various forms, such as in the form of liquids, creams, gels or any other form which is suitable for dyeing keratin fibres, and in particular human hair.

Another subject of the invention is a multi-compartment device or dyeing kit or any other multi-compartment packaging system, comprising at least two compartments, a first compartment of which contains the dye composition as defined above and a second compartment of which contains the oxidizing composition as defined above. These devices may preferably be equipped with a means which makes it possible to deliver the desired mixture onto the hair, such as the devices described in French patent FR-2,586,913 which is incorporated herein by reference.

The examples which follow are intended to illustrate the invention without, however, limiting the scope thereof.

EXAMPLES

The following dye compositions 1 to 5 were prepared:

| COMPOSITION | 1(*) | 2(*) | 3(*) | 4() | 5() |
|---|---|---|---|---|---|
| Para-phenylenediamine (in moles) | $3 \times 10^{-3}$ | $3 \times 10^{-3}$ | $3 \times 10^{-3}$ | $3 \times 10^{-3}$ | $3 \times 10^{-3}$ |
| 3-Aminophenol (in moles) | $3 \times 10^{-3}$ | | | $1.5 \times 10^{-3}$ | |
| 5-Amino-2-methylphenol (in moles) | | $3 \times 10^{-3}$ | | | $1.5 \times 10^{-3}$ |
| 6-Hydroxyindoline hydrochloride (in moles) | | | $3 \times 10^{-3}$ | $1.5 \times 10^{-3}$ | $1.5 \times 10^{-3}$ |
| Common dye support | (*) | (*) | (*) | (*) | (***) |
| Demineralized water qs | 100 g | 100 g | 100 g | 100 g | 100 g |

(*): dye composition not forming part of the invention
(**): dye composition in accordance with the invention
(***): Common dye support:

| | |
|---|---|
| Oleyl alcohol polyglycerolated with 2 mol of glycerol | 4.0 g |
| Oleyl alcohol polyglycerolated with 4 mol of glycerol, containing 78% of active material (AM) | 5.69 g AM |
| Oleic acid | 3.0 g |
| Oleylamine containing 2 mol of ethylene oxide, sold under the trade name Ethomeen O12 by the company AKZO | 7.0 g |
| Diethylaminopropyl laurylaminosuccinamate, sodium salt, containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution, containing 35% of AM | 0.455 g AM |
| Ammonium acetate | 0.8 g |
| Antioxidant, sequestering agent | qs |
| Fragrance, preserving agent | qs |
| Aqueous ammonia containing 20% of $NH_3$ | 10.0 g |

Each dye composition 1 to 5 was mixed, at the time of use, with an equal weight amount of 20-volume aqueous hydrogen peroxide solution (6% by weight).

Each resulting mixture was applied for 30 minutes, on the one hand, to locks of natural grey hair containing 90% of white hairs (lock no. 1 of non-sensitized hair) and, on the other hand, to a lock of the same grey hair containing 90% white hairs but which had undergone permanent-waving (lock no. 2 of sensitized hair). The locks of hair were then rinsed, washed with a standard shampoo and then dried.

The color of the locks was then evaluated in the Munsell system using a Minolta CM 2002 colorimeter.

According to the Munsell notation, a color is defined by the expression H V/C in which the three parameters respectively denote the shade or Hue (H), the intensity or Value (V) and the purity or Chromaticity (C), the oblique line in this expression simply being a convention and not indicating a ratio.

The difference in color between two locks is calculated by applying the Nickerson formula:

$$\Delta E = 0.4 \, C_0 \Delta H + 6 \Delta V + 3 \Delta C,$$

as described, for example, in "Couleur, Industrie et Technique"; pages 14–17; vol. No. 5; 1978.

In this formula, $\Delta E$ represents the difference in color between two locks, $\Delta H$, $\Delta V$ and $\Delta C$ represent the variation in absolute value of the parameters H, V and C, and $C_0$ represents the purity of the lock relative to which it is desired to evaluate the difference in color.

The difference in color between natural (non-sensitized) hair and permanent-waved (sensitized) hair made it possible to demonstrate the selectivity of each of the dye compositions 1 to 5 and was calculated by applying the Nickerson formula.

The results are featured in the table below:

| EXAMPLE (COMPOSITION) | Colour on natural hair | Colour on permanent-waved hair | Difference in colour (selectivity) | | | |
|---|---|---|---|---|---|---|
| | | | ΔH | ΔV | ΔC | ΔE |
| 1 (1) | 8.2 RP 2.7/1.6 | 0.8 R 2.3/1.3 | 2.6 | 0.4 | 0.3 | 5.0 |
| 2 (2) | 8.3 RP 3.0/3.3 | 8.8 RP 2.5/3.8 | 0.5 | 0.5 | 0.5 | 5.2 |
| 3 (3) | 4.6 R 3.1/1.4 | 7.8 RP 2.8/1.6 | 6.8 | 0.3 | 0.2 | 6.2 |
| 4 (4) | 0.9 R 2.9/1.5 | 1.3 R 2.7/1.5 | 0.4 | 0.2 | 0 | 1.4 |
| 5 (5) | 9.9 RP 2.9/2.0 | 9.8 RP 2.5/2.0 | 0.1 | 0.4 | 0 | 2.5 |

These results clearly show that the dye compositions 4 and 5 which are in accordance with the invention, that is to say compositions comprising an oxidation base (para-phenylenediamine) in combination with a meta-aminophenol as a first coupler and 6-hydroxyindoline hydrochloride as a second coupler, lead to very unselective, i.e., low selectivity, colorations. On the other hand, the comparative dye compositions of Examples 1 to 3 (which do not form part of the invention since they contain only one of the two couplers) lead to markedly more selective, i.e., higher selectivity, colorations.

What is claimed is:

1. A composition for the oxidation dyeing of keratin fibres, said composition comprising, in a medium which is suitable for dyeing:

at least one oxidation base selected from para-phenylenediamines, acid addition salts of said para-phenylenediamines, bis(phenyl)alkylenediamines, and acid addition salts of said bis(phenyl)alkylenediamines, at least one first coupler selected from meta-aminophenols and the acid addition salts of said meta-aminophenols, and at least one second coupler selected from 6-hydroxyindoline and the acid addition salts of said 6-hydroxyindoline, wherein said at least one oxidation base, said at least one first coupler, and said at least one second coupler are present in amounts effective to oxidatively dye said keratin fibres.

2. A composition according to claim 1, wherein said at least one first coupler is selected from compounds of formula (I), and the acid addition salts of said compounds:

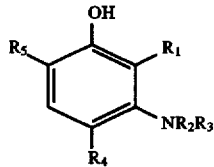

in which:

$R_1$ and $R_4$ which may be identical or different, represent a hydrogen or halogen atom or a $C_1$–$C_4$ alkyl or $C_1$–$C_4$ alkoxy radical; $R_2$ represents a hydrogen atom or a $C_1$–$C_4$ alkyl, $C_1$–$C_4$ monohydroxyalkyl, $C_2$–$C_4$ polyhydroxyalkyl, $C_1$–$C_4$ trifluoroalkyl or carbamoylmethyl radical; $R_3$ represents a hydrogen atom or a $C_1$–$C_4$ alkyl radical or forms, with $R_2$ and the nitrogen atom to which they are attached, a 5- or 6-membered heterocycle; and $R_5$ represents a hydrogen or halogen atom or a $C_1$–$C_4$ alkyl, $C_1$–$C_4$ alkoxy, $C_1$–$C_4$ monohydroxyalkyl or $C_2$–$C_4$ polyhydroxyalkyl radical.

3. A composition according to claim 2, wherein said meta-aminophenols of formula (I) are selected from 3-aminophenol, 5-amino-2-methoxyphenol, 5-amino-4-chloro-2-methylphenol, 5-amino-2,4-dimethoxyphenol, 5-amino-2-β-hydroxyethyloxyphenol, 5-N-(β-hydroxyethyl)amino-4-methoxy-2-methylphenol, 5-amino-4-methoxy-2-methylphenol, 5-N-(γ-hydroxypropyl)amino-2-methylphenol, 5-N-(β-hydroxyethyl)amino-2-methylphenol, 5-amino-2-methylphenol, 3-N-(carbamoylmethyl)aminophenol, 5-N-(carbamoylmethyl)amino-2-methylphenol, 3-N,N-(dimethyl)aminophenol, 3-N,N-(diethyl)aminophenol, 3-amino-2,4-dichlorophenol, 3-amino-4,6-dichlorophenol, 5-amino-6-chloro-2-methylphenol, 2-chloro-5-N-(2',2',2'-trifluoroethyl)aminophenol, 5-amino-4-chloro-2-methylphenol, 3-N-(cyclopentyl)-aminophenol, and the acid addition salts of said compounds.

4. A composition according to claim 1, wherein said para-phenylenediamines are selected from compounds of formula (II), and the acid addition salts of said compounds:

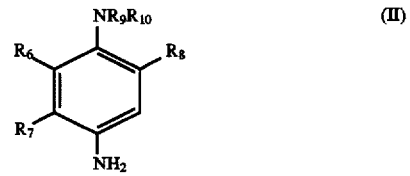

in which:

$R_6$, $R_7$ and $R_8$, which may be identical or different, represent a hydrogen or halogen atom or a $C_1$–$C_4$ alkyl, $C_1$–$C_4$ alkoxy, sulpho, carboxyl, $C_1$–$C_4$ monohydroxyalkyl or $C_2$–$C_4$ polyhydroxyalkyl radical; $R_9$ and $R_{10}$, which may be identical or different, represent a hydrogen atom, a $C_1$–$C_4$ alkyl, $C_1$–$C_4$ monohydroxyalkyl, $C_2$–$C_4$ polyhydroxyalkyl, ($C_1$–$C_4$)alkoxy($C_1$–$C_4$)alkyl, $C_1$–$C_4$ carbamylalkyl, $C_1$–$C_4$ mesylaminoalkyl, $C_1$–$C_4$ acetylamino-alkyl, $C_1$–$C_4$ ureidoalkyl, ($C_1$–$C_4$) carbalkoxy($C_1$–$C_4$)aminoalkyl, $C_1$–$C_4$ sulphoalkyl, $C_1$–$C_4$ piperidinoalkyl, $C_1$–$C_4$ morpholinoalkyl or phenyl radical or a phenyl radical substituted in the para position with an amino group, or $R_9$ and $R_{10}$ form, together with the nitrogen atom to which they are attached, a piperidino or morpholino heterocycle;

with the proviso that if $R_9$ and $R_{10}$ do not simultaneously represent a hydrogen atom, then at least one of the radicals $R_6$ and $R_8$ must represent a hydrogen atom.

5. A composition according to claim 4, wherein said para-phenylenediamines of formula (II) are selected from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 4-amino-N-ethyl-N-(carbamylmethyl)aniline, 4-amino-3-methyl-N-ethyl-N-(carbamylmethyl)aniline, 4-amino-N-ethyl-N-(β-piperidinoethyl)aniline, 4-amino-3-methyl-N-ethyl-N-(β-piperidinoethyl)aniline, 4-amino-N-ethyl-N-(β-morpholinoethyl)aniline, 4-amino-3-methyl-N-ethyl-N-(β-morpholinoethyl)aniline, 4-amino-N-ethyl-N-(β-acetylaminoethyl)aniline, 4-amino-N-(β-methoxyethyl) aniline, 4-amino-3-methyl-N-ethyl-N-(β-acetylaminoethyl) aniline, 4-amino-N-ethyl-N-(β-mesylaminoethyl)aniline, 4-amino-3-methyl-N-ethyl-N-(β-mesylaminoethyl)aniline, 4-amino-N-ethyl-N-(β-sulphoethyl)aniline, 4-amino-3-methyl-N-ethyl-N-(β-sulphoethyl)aniline, N-[(4'-amino) phenyl]morpholine, N-[(4'-amino)phenyl]piperidine, 2-β-hydroxyethyl-para-phenylenediamine, 2-fluoro-para-phenylenediamine, 2-carboxy-para-phenylenediamine, 2-sulpho-para-phenylenediamine, 2-isopropyl-para-phenylenediamine, 2-n-propyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, and the acid addition salts of said compounds.

6. A composition according to claim 5, wherein said para-phenylenediamines of formula (II) are selected from para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine and 4-amino-N-(β-methoxyethyl)aniline and the acid addition salts of said compounds.

7. A composition according to claim 1, wherein said bis(phenyl)alkylene-diamines are selected from compounds of formula (III), and the acid addition salts of said compounds:

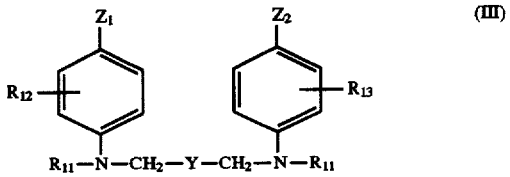

in which:

Z$_1$ and Z$_2$, which may be identical or different, represent a hydroxyl radical or a radical NHR$_{14}$ in which R$_{14}$ represents a hydrogen atom or a C$_1$-C$_4$ alkyl radical; each R$_{11}$ independently represents a hydrogen atom, a C$_1$-C$_4$ alkyl, C$_1$-C$_4$ monohydroxyalkyl or C$_2$-C$_4$ polyhydroxyalkyl radical or a C$_1$-C$_4$ aminoalkyl radical in which the amino residue may be substituted; R$_{12}$ and R$_{13}$, which may be identical or different, represent a hydrogen or halogen atom or a C$_1$-C$_4$ alkyl radical; and Y represents a radical, said radical being —(CH$_2$)—; —(CH$_2$)$_m$—O—(CH$_2$)$_m$—; —(CH$_2$)$_m$—CHOH—(CH$_2$)$_m$—; or —(CH$_2$)$_m$—N—(CH$_2$)$_m$—;
　　　　　|
　　　　　CH$_3$ in which n is an integer ranging from 0 to 8 inclusively and each m is independently an integer ranging from 0 to 4 inclusively.

8. A composition according to claim 7, wherein said bis(phenyl)alkylenediamines of formula (III) are selected from N,N'-bis(β-hydroxyethyl)-N,N'-bis(4'-aminophenyl)-1,3-diaminopropanol, N,N'-bis(βhydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and the acid addition salts of said compounds.

9. A composition according to claim 1, wherein said acid addition salts are selected from hydrochlorides, hydrobromides, sulphates and tartrates.

10. A composition according to claim 1, wherein said at least one oxidation base selected from para-phenylenediamines, acid addition salts of said para-phenylenediamines, bis(phenyl)alkylenediamines, and acid addition salts of said bis(phenyl)alkylenediamines represents from 0.0005 to 12% by weight relative to the total weight of the dye composition.

11. A composition according to claim 10, wherein said at least one oxidation base selected from para-phenylenediamines, acid addition salts of said para-phenylenediamines, bis(phenyl)alkylenediamines, and acid addition salts of said bis(phenyl)alkylenediamines represents from 0.005 to 6% by weight relative to the total weight of the dye composition.

12. A composition according to claim 1, wherein said at least one first coupler represents from 0.0001 to 10% by weight relative to the total weight of the dye composition.

13. A composition according to claim 12, wherein said at least one first coupler represents from 0.005 to 5% by weight relative to the total weight of the dye composition.

14. A composition according to claim 1, wherein said at least one second coupler represents from 0.0001 to 5% by weight relative to the total weight of the dye composition.

15. A composition according to claim 14, wherein said at least one second coupler represents from 0.005 to 3% by weight relative to the total weight of the dye composition.

16. A composition according to claim 1, wherein said medium suitable for dyeing comprises water or a mixture of water and at least one organic solvent selected from C$_1$-C$_4$ lower alkanols, glycerol, glycols and glycol ethers, aromatic alcohols and mixtures thereof.

17. A composition according to claim 1, which composition has a pH ranging from 3 to 12.

18. A process for dyeing keratin fibres, said process comprising the steps of:
　applying to said fibres at least one dyeing composition according to claim 1 in an amount effective to develop a coloration; and
　developing said coloration at acidic, neutral or alkaline pH by adding an effective amount of an oxidizing agent to said at least one dyeing composition at the time said at least one dyeing composition is applied to said fibres or by separately applying an oxidizing composition comprising an effective amount of an oxidizing agent to said fibres, either at the same time that said at least one dyeing composition is applied or sequentially with said at least one dyeing composition.

19. A process according to claim 18, wherein said oxidizing agent is selected from hydrogen peroxide, urea peroxide, alkali metal bromates and persalts.

20. A process according to claim 19, wherein said persalts are perborates or persulphates.

21. A multi-compartment device or multi-compartment dyeing kit comprising at least two compartments, wherein a first compartment contains a composition as retired in claim 1 and a second compartment contains an oxidizing composition.

* * * * *

UNITED STATES PATENT AND TRADEMARK OFFICE
CERTIFICATE OF CORRECTION

PATENT NO.   : 5,735,909
DATED        : April 7, 1998
INVENTOR(S)  : Mireille Maubru It is certified that error appears in the above-identified patent and that said Letters Patent is hereby corrected as shown below:

On the title page: ITEM [54] and Column 1, line 1, "COMPOSITIONS" should read --COMPOSITION--.

Claim 7, column 11, line 44, "bis(phenyl)alkylene-diamines" should read --bis(phenyl)alkylenediamines--.

Claim 8, column 12, line 15, "(Bhydroxyethyl)" should read --(B-hydroxyethyl)--.

Claim 21, column 14, line 5, "retired" should read --recited--.

Signed and Sealed this

Twenty-first Day of July, 1998

Attest:

BRUCE LEHMAN

*Attesting Officer*   *Commissioner of Patents and Trademarks*